United States Patent
Sharma et al.

(10) Patent No.: US 8,785,691 B2
(45) Date of Patent: Jul. 22, 2014

(54) DIALKYLDIAZA-TETRAALKYLOCTANE DIAMIDE DERIVATIVES USEFUL FOR THE SEPARATION OF TRIVALENT ACTINIDES FROM LANTHANIDES AND PROCESS FOR THE PREPARATION THEREOF

(75) Inventors: Joti Nath Sharma, Mumbai (IN); Ritesh Ruhela, Mumbai (IN); Smitha Manohar, Mumbai (IN); Piaray Kishen Wattal, Mumbai (IN); Ashok Kumar Suri, Mumbai (IN)

(73) Assignee: Secretary, Department of Atomic Energy, Mumbai, Maharashtra (IN)

( * ) Notice: Subject to any disclaimer, the term of this patent is extended or adjusted under 35 U.S.C. 154(b) by 138 days.

(21) Appl. No.: 13/388,000

(22) PCT Filed: Sep. 11, 2009

(86) PCT No.: PCT/IN2009/000499
§ 371 (c)(1),
(2), (4) Date: Mar. 23, 2012

(87) PCT Pub. No.: WO2011/024184
PCT Pub. Date: Mar. 3, 2011

(65) Prior Publication Data
US 2012/0172626 A1    Jul. 5, 2012

(30) Foreign Application Priority Data
Jul. 30, 2009   (IN) .................. 1748/MUM/2009

(51) Int. Cl.
C07C 237/02    (2006.01)
C07C 237/06    (2006.01)
C07C 231/12    (2006.01)

(52) U.S. Cl.
CPC ............ C07C 237/02 (2013.01); C07C 237/06 (2013.01); C07C 231/12 (2013.01)
USPC ...................................................... 564/160

(58) Field of Classification Search
CPC ........................... C07C 237/06; C07C 231/02
USPC ...................................................... 564/160
See application file for complete search history.

(56) References Cited

U.S. PATENT DOCUMENTS
4,461,747 A   7/1984  Fitoussi et al.
4,496,523 A   1/1985  Bonnin et al.

FOREIGN PATENT DOCUMENTS
EP   1 923 473    5/2008
FR   2 810 679    12/2001

OTHER PUBLICATIONS

Borowitz et al., "The Preparation and Properties of Neutral Diamide Ionophores for Group IIA Metal Cations—II", Tetrahedron, vol. 40, No. 6, 1984, pp. 1009-1016.
Drew et al., "6,6'-bis-(5,6-diethyl-[1,2,4]triazin-3-yl)-2,2'-bipyridyl the First Example of a New Class of Quadridentate Heterocyclic Extraction Reagents for the Separation of Americium(III) and Europium(III)", Inorganic Chemicstry Communications, vol. 8, 2005, pp. 239-241.
Erne et al., "237. Lipophilic Aides of EDTA, NTA and Iminodiacetic Acid as Ionophores for Alkaline Earth Metal Cations", Helvetica Chimica Acta, vol. 63, No. 8, 1980, pp. 2264-2270.
Gatrone et al., "The Synthesis and Purification of the Carbamoylmethylphosphine Oxides", Solvent Extraction and Ion Exchange, vol. 5, No. 6, 1987, pp. 1075-1116.
Kolarik et al., "Extraction of Am(III) and Eu(III) Nitrates by 2-6-di-(5,6-dipropyl-1,2,4-triazin-3-yl)pyridines 1", Solvent Extraction and Ion Exchange, vol. 17, No. 5, 1999, pp. 1155-1170.
Matsumura et al., "Extraction Behavior of Am(III) from Eu(III) with Hydrophobic Derivatives of N,N,N',N'-tetrakis(2-methylpyridyl)ethylenediamine (TPEN)", Journal of Nuclear Science and Technology, vol. 43, No. 7, 2006, pp. 824-827.
Modolo et al., "Synergistic Selective Extraction of Actinides(III) over Lanthanides from Nitric Acid Using New Aromatic Diorganyldithiophosphinic Acids and Neutral Organophosphorus Compounds", Solvent Extraction and Ion Exchange, vol. 17, No. 1, 1999, pp. 33-53.
Readio et al., "Metal Complexes of $N,N,N^1,N^1$-tetrakis-($n$-propyl)-1,2-phenylenedioxydiacetamide and Related Ligands", J. Coord. Chem., vol. 11, 1981, pp. 135-142.

(Continued)

Primary Examiner — Shailendra Kumar
(74) Attorney, Agent, or Firm — Merchant & Gould P.C.

(57) ABSTRACT

The novel lipophilic metal extractants of the class dialkyl-diaza-tetraalkyloctanediamide (DADA) useful to selectively separate trivalent americium (sup. 241 Am) from trivalent lanthanides are represented by the formula 1:

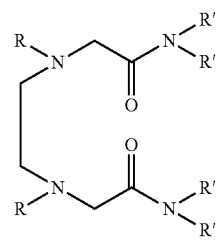

Wherein R is a $C_1$ to $C_5$ normal alkyl and R' is a $C_4$ to $C_8$ normal and branched alkyl group. The compounds are synthesized at high yield and purity by the reaction of corresponding N,N'-dialkylethylenediamine and N,N-dialkyl-2-chloroacetamide. The separation is achieved by utilizing the soft-soft interaction between the trivalent actinides and 'N' atoms of the extractant. Both soft donor "n" and hard donor 'O' sites are incorporated in the molecule for better extraction of trivalent actinides over trivalent lanthanides. Thus, this molecule can be used as selective extractant to separate trivalent actinides from trivalent lanthanides.

3 Claims, No Drawings

(56) References Cited

OTHER PUBLICATIONS

Sasaki et al., "Extraction of Actinides(III), (IV), (V), (VI) and Lanthanides(III) by Structurally Tailored Diamides", *Solvent Extraction And Ion Exchange*, vol. 20, No. 1, 2002, pp. 21-34.

Sasaki et al., "The Novel Extractants, Diglycolamides, for the Extraction of Lanthanides and Actinides in $HNO_3$-*n*-dodecane System", *Solvent Extraction and Ion Exchange*, vol. 19, No. 1, 2001, pp. 91-103.

Zhu et al., "Extraction of Am(III) and Eu(III) from Nitrate Solution with Purified Cyanex 301", *Solvent Extraction and Ion Exchange*, vol. 14, No. 1, 1996, pp. 61-68, 2007.

Zhu, "The Separation of Americium from Light Lanthanides by Cyanex 301 Extraction", Institute of Nuclear Energy Technology, Tsinghua University, Beijing, China, 1994, pp. 95-98.

DIALKYLDIAZA-TETRAALKYLOCTANE DIAMIDE DERIVATIVES USEFUL FOR THE SEPARATION OF TRIVALENT ACTINIDES FROM LANTHANIDES AND PROCESS FOR THE PREPARATION THEREOF

This application is a National Stage Application of PCT/IN2009/000499, filed 11 Sep. 2009, which claims benefit of Serial No. 1748/MUM/2009, filed 30 Jul. 2009 in India and which applications are incorporated herein by reference. To the extent appropriate, a claim of priority is made to each of the above disclosed applications.

FIELD OF THE INVENTION

The present invention relates to a novel lipophilic extractant, its preparation process and its use in selective separation of trivalent actinides from lanthanides.

More particularly, the present invention relates to a novel lipophilic extractant of the class dialkyldiaza-tetraalkyloctanediamides, for the separation of trace concentration of trivalent americium ($^{241}$Am) from macro amount of trivalent lanthanides from aqueous radioactive waste streams.

BACKGROUND AND PRIOR ART

Reprocessing of spent fuel by the PUREX process leads to generation of high-level liquid waste (HLLW). Presences of the long-lived minor actinides in the waste essentially determine its long-term hazard potential. Keeping in view of the long-term strategy for the management of the waste, it is desirable that the waste be subjected to partitioning to devoid the actinides from HLLW. This technology will pave the way for subjecting the actinides either to transmutation or immobilizing them in suitable host materials for their long term management.

The presently known processes as TRUEX, DIAMEX and solvents such as TRPO, diglycolamides made it possible to extract trivalent actinides in organic solvents from HLLW. But in all these processes trivalent lanthanides resulting from the fission were also extracted along with actinides in the organic phase. The back extraction of the organic phase results in the aqueous phase containing both the trivalent actinides and lanthanides. However, in order to further improve the control of waste materials, it would be of vital interest to separate minor actinides from lanthanides. Accordingly, efficient separation processes continue to be sought, and this is the context in which most current researches on ligand design were being carried out.

Group separation of trivalent actinides from lanthanides is difficult because they tend to form similar coordination complexes with ligands due to their similar charge densities. These separations however, can be accomplished by utilizing the fact that a small degree of covalency in the bond between actinide-ligands exists over lanthanide ligands. The increased covalency results in actinide elements having slightly higher affinity for soft donor ligands having N and S donor atoms. Using this principle various extractants have been developed.

The sulphur containing extractants like dithiophosphoric acid, bis(2,4,4,trimethyl pentyl)dithiophosphinic acid and bis (dichlorophenyl)dithiophosphinic acid are described by C. Musikas, G. Le Marios, R. Fitoussi and C. Cuillerdier, Actinide separations, ACS Symposium Series, Vol. 117, 1980; R. Fitoussi, C. Musikas, U.S. Pat. No. 4,461,747; Y. Zhu, Radiochimica Acta, 68, 95-98, 1995; Y. Zhu, J. Chen and Rongzhou Jiao, Solv. Extr. Ion Exch. 14(1), 61-68, 1996; G. Modolo, R. Odoj. Solv. Extr. Ion. Exch., 17 (1), 33-53, 1999. However, their susceptibility to degradation under process conditions limits their use.

Nitrogen containing extractants like TPTZ, nPr-BTP, and TPEN are described by M. Bonnin, C. Musikas, P. Vitorge, U.S. Pat. No. 4,496,523, 1985; Z. Kolarik, U. Mullich, F. Gassener, Solv. Extr. Ion Exch., 17(5), 1155-1170, 1999: T. Matsumura and K. Takeshita, J. Nuc, Sci. Tech., 43, 7, 824-827, nPr-BTP and their derivatives are superior in selectivity and efficiency, however their performance is reduced due to degradation during practical use. TPTZ and TPEN alone have weak interaction with trivalent actinides and used in a synergistic combination with a lipophillic cation exchanger having hard donor oxygen atom for better extractability.

Thus there is a need to provide an extractant, which overcomes the problems of the compounds as taught in the prior art.

The present inventors have found that the subject compounds of the present invention differ entirely by their chemical structure where both soft donor nitrogen atoms and hard donor oxygen atoms are incorporated in the molecule to attain the separation without use of second extracting agent. The numbers and positions of donor atoms in the molecule are appropriately integrated in order to meet the requirements of favorable complex formation with trivalent actinides over lanthanides.

OBJECTS OF THE INVENTION

It is an object of the present invention to overcome the drawbacks of the prior art.

It is another object of the present invention to provide a novel lipophilic extractant for separation of trivalent actinides from lanthanides.

Another object of the present invention is to provide a novel lipophillic extractant for separation of traces concentration of trivalent americium ($^{241}$Am) from macro amount of trivalent lanthanides from aqueous radioactive waste streams.

Yet another object of the present invention is to provide a process for the preparation of the novel lipophillic extractant.

SUMMARY OF THE INVENTION

Accordingly, the present invention relates to a lipophillic extractant capable of selectively extracting trivalent actinides from lanthanide ions, represented by the following structural formula 1,

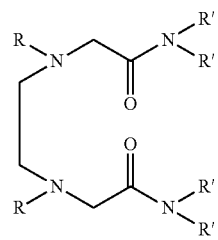

wherein R is a $C_1$ to $C_5$ normal alkyl and R' is a $C_4$ to $C_8$ normal and branched alkyl group.

Another aspect of the present invention is to provide A process for the preparation of lipophillic extractant of formula 1,

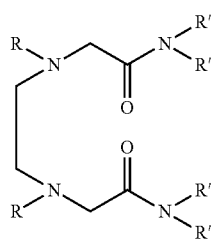

wherein R is a $C_1$ to $C_5$ normal alkyl and R' is a $C_4$ to $C_8$ normal and branched alkyl group wherein said process comprises the steps of:
(i) condensing one mole of N,N'-dialkylethylenediamine of the structural formula 2 with 2.2 to 5.0 moles of N,N-dialkyl-2-chloroacetamide of the structural formula 3 in the presence of 2.2 to 10 moles of triethylamine.
(ii) diluting the reaction mixture with xylene and neutralizing with 1.0M hydrochloric acid;
(iii) separation of the organic phase and washing with water and 2.0% sodium carbonate solution and further washed with water to neutral pH.
(iv) drying the organic phase with anhydrous sodium sulphate and concentrated by distillation under reduced pressure.
(v) distillation of the residue at 120° C. under vacuum of about 1.0 millitorr using centrifugal molecular distillation unit to remove the unreacted N,N-dialkyl-2-chloroacetamide.
(vi) obtaining the product as residue having a purity of about 96%.
(vii) Characterization of the compound by elemental analyzer, GC-MS and NMR.

DETAIL DESCRIPTION OF THE INVENTION

Accordingly, the present invention to a novel lipophillic extractant of the class dialkyldiaza-tetraalkyloctanediamides and the preparation of the compound of structural formula 1:

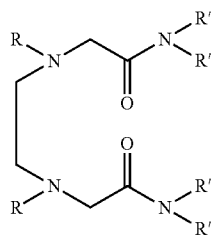

According to the present invention, the novel lipophillic extractant is prepared by the following process comprising the steps of condensing One mole of N,N'-dialkylethylenediamine of the structural formula 2 with 2.2 to 5.0 moles of N,N-dialkyl-2-chloroacetamide of the structural formula 3, in the presence of 2.2 to 10 moles of triethylamine. The reaction was carried out at 60-85° C. for 48 hrs in $N_2$ atmosphere. The overall synthesis scheme is shows as under:

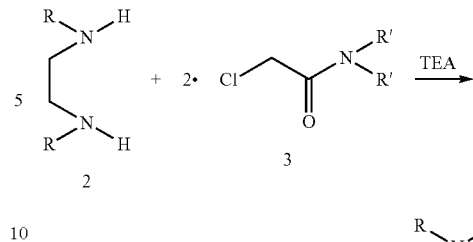

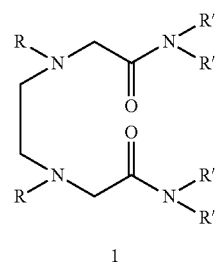

On cooling the reaction mixture is diluted with xylene and neutralized with 1.0M hydrochloric acid. The organic phase is separated and washed with water and 2.0% sodium carbonate solution and further washed with water to neutral pH. The organic phase is dried with anhydrous sodium sulphate and concentrated by distillation under reduced pressure. The residue is further distilled at 120° C. under vacuum of about 1.0 millitorr using centrifugal molecular distillation unit to remove the unreacted N,N-dialkyl-2-chloroacetamide. The product obtained as residue is having a purity of about 96%. The overall yield of the process was about 40 to 90%. The compound is characterized by elemental analyzer, GC-MS and NMR.

The compounds of the structural formula 2 and formula 3 are prepared as per procedure given in Beil 6 (4), 3529 and Solv. Extr. Ion Exch., 5, 6, 1075 (1987) respectively.

The exemplary compounds of structural formula 1, synthesized in this invention are as under:

N,N,N',N'-tetra isobutyl-3,6(N",N"'dimethyl)diaza-octane 1,8 diamide;
N,N,N',N'-tetra hexyl-3,6(N",N"'dimethyl)diaza-octane 1,8 diamide;
N,N,N',N'-tetra(2-ethylhexyl)-3,6(N",N"'dimethyl)diaza-octane 1,8 diamide;
N,N,N',N'-tetra isobutyl-3,6(N",N"'diethyl)diaza-octane 1,8, diamide;
N,N,N',N'-tetra hexyl-3,6(N",N"'diethyl)diaza-octane 1,8 diamide;
N,N,N',N'-tetra(2-ethylhexyl)-3,6(N",N"'diethyl)diaza-octane 1,8 diamide;
N,N,N',N'-tetra isobutyl-3,6(n", N"'dipropyl)diaza-octane 1,8 diamide;
N,N,N',N'-tetra hexyl-3,6(N",N"'dipropyl)diaza-octane 1,8 diamide;
N,N,N',N'-tetra(2-ethylhexyl)-3,6(N",N"'dipropyl)diaza-octane 1,8 diamide;
N,N,N'N'-tetra isobutyl-3,6(N",N"'dibutyl)diaza-octane 1,8 diamide;
N,N,N',N'-tetra hexyl-3,6(N",N"'dibutyl)diaza-octane 1,8 diamide;
N,N,N',N'-tetra(2-ethylhexyl)-3,6(N",N"'dibutyl)diaza-octane 1,8 diamide;
N,N,N',N'-tetra isobutyl 1-3,6(N",N"'dipentyl)diaza-octane 1,8 diamide;
N,N,N',N'-tetra hexyl-3,6(N",N"'dipentyl)diaza-octane 1,8 diamide;

N,N,N',N'-tetra(2-ethylhexyl)-3,6(N'',N'''dipentyl)diaza-octane 1,8 diamide.

Among these, the most preferred compounds are N,N,N',N'-tetra(2-ethylhexyl)-3,6(N'',N'''dibutyl)diaza-octane 1,8 diamide and N,N,N'N'-tetra(2-ethylhexyl)-3,6(N'',N'''dipentyl)diaza-octane 1,8 diamide. The lower alkyl derivatives of diazadiamide R=$C_1$ to $C_3$ and R'=isobutyl and hexyl, are found to be either hydrophilic in nature or have excessive tendency to form crud in acidic medium. Therefore, during various steps of synthesis and workup, they could not be obtained in better yields. The higher homologues of diazadiamide, where R is $C_6$ and above could not be synthesized in better yields under the similar conditions of reactions. This could be due to large steric hindrance and electronic effect imparted by alkyl group of ethylenediamine moiety which slows down the condensation with amidic moiety.

The preferred compounds have desirable lipophilicity to use it as extractant and diluted in 1-octanol for its effective use. The concentration of 0.1M extractant in 1-octanol was found to be optimum for achieving the workable separation between trivalent actinides and lanthanides.

The extraction is performed by contacting aqueous phase containing both trivalent actinides and lanthanides with organic phase at the phase ratio of 1:1. After agitation for 30 minutes and separation of two phases, the metal ion content of each phase is measured to determine the distribution co-efficient of each of metal ions. All the extraction experiments are performed at ambient conditions of temperature and pressure. The concentration of americium was determined by gamma spectrometry and lanthanides (Ln's) by ICP-AES analysis.

The distribution coefficient DM of a metal is determined as a ratio of concentration of the metal in the organic phase to the aqueous phase. The separation factor is calculated by determining DAm and DLn's in the presence of each other and defined as DAm/DLn's.

Maximum extraction is obtained in the pH range of 2.0 to 3.0 Complete stripping of the actinide from the loaded organic phase was achieved using 0.5M nitric acid. During the stripping process nitric acid replaces the actinide nitrate from the complex. The reuse of the solvent is done by neutralizing the solvent with 2.0% sodium carbonate solution. The extraction, stripping and reuse of the solvent are shown by the following equations:

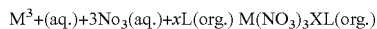

$M^{3+}$(aq.)+$3No_3$(aq.)+xL(org.) M$(NO_3)_3$XL(org.)

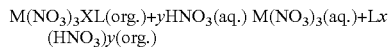

M$(NO_3)_3$XL(org.)+yHNO$_3$(aq.) M$(NO_3)_3$(aq.)+Lx(HNO$_3$)y(org.)

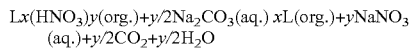

Lx(HNO$_3$)y(org.)+y/2Na$_2$CO$_3$(aq.) xL(org.)+yNaNO$_3$(aq.)+y/2CO$_2$+y/2H$_2$O A better understanding of the present invention can be obtained from the study of the following illustrative and non-limitative examples.

Example 1

Synthesis of N,N,N',N'-tetra(2-ethylhexyl)-3,6(N'',N'''dibutyl)diaza-octane 1,8 diamide 209 ml (1.0 mol) of N,N'-dibutylethylenediamine, 785 ml (2.45 mol) of N,N-(2-ethylhexyl)-2-chloroacetamide and 900 ml (6.45 mol) of triethylamine are mixed together and well stirred at room temperature under nitrogen atmosphere. The temperature of the reaction mixture is slowly raised and refluxed at 85° C. for 48 hours under vigorous stirring. The progress of the reaction was monitored by GC-MS. On cooling the reaction mixture is diluted with xylene and neutralized with 1.0M hydrochloric acid. The organic phase is separated and washed with water and 2.0% sodium carbonate solution and further washed with water to neutral pH. The organic is dried with anhydrous sodium sulphate and concentrated by distillation under reduced pressure. The residue is further distilled at 140° C. under vacuum of about 1.0 millitorr using centrifugal molecular distillation unit to remove the unreacted N,N-(2-ethylhexyl)-2-chloroacetamide almost completely. The product obtained as thick viscous oily residue is having a purity of about 96% (GC-MS). The overall yield of the process is about 90%. The compound is characterized by elemental analyzer, GC-MS and NMR.

GC-MS is performed on Shimadzu GCMS-QP2010 plus instrument with a single quadrupole mass spectrometer at 70 eV using 10 m×0.25 mm CP-Sil5CB fused silica capillary column. Helium is the carrier and the temperature program was 60° C. for 1 minute, increased at 280° C. at 10° C. per minute and held at 280° C. for 20 minutes. The injector temperature was 300° C.

GC-MS: 10.79 min., 0.76%, m/z 318 calculated for ClCH2CON(C8H17)2; 12.88 min., 0.47%, m/z 354 calculated for (C4H9)NHCH2CON(C8H17)2; 20.184 min., 2.36%, m/z 635 calculated for C8H17)2NC(O)CH2N(C4H9)(CH2)2N(C4H9)CH2C(O)N(CH3)C8H17; 22.59 min., 96.10%, m/z 734 calculated for (C8H17)2NC(O)CH2N(C4H9) (CH2)2N(C4H9)-CH2C(O)N(C8H17)2.

Elemental analysis for $C_{46}H_{94}O_2N_4$

Calculated: C, 75.14; H, 12.88; O, 4.35; N, 7.61

Found: C, 75.28; H, 12.80), 4.23; N, 7.69

NMR spectra of DADA appropriately dissolved in CDCl$_3$ are measured on a Brucker AV 500 spectrometer at 500 MHZ with TMS as an internal reference.

Nuclear magnetic resonance spectra of proton has shown a singlet peak over 3.644-3.541 ppm for four protons of two methylene groups, multiplet peak over 3.283-3.166 ppm for eight protons of two —NCH2CH2- groups, singlet peak over 2.977-2.895 ppm for four protons of —NCH2CH2N— group, multiplet over 1.627-1.464 ppm for eight protons of four —CO—N—CH2- groups, multiplet over 1.351-1.120 ppm for forty protons of four —CH(C2H5)CH2-CH2- groups and the multiplet peak over 0.872-0.818 ppm for thirty protons of six —CH2CH3 groups.

$^{13}$C NMR: 169.0 ppm for C═O group, 77.641-76.364 ppm for —CH2- of —N—CH2-CO—, 55.158, 52.022, 50.023, 47.706 ppm for —N—C of amidic group, 37.562, 36.217 ppm for —N—CH2-CH2-N—, 30.089, 28.230 ppm for —N—CH2—23.352, 22.662, 22.597, 19.594, 13.625, 10.567 and 10.108 ppm for rest of the —CH2-CH2- and —CH2-CH3.

Example II to VI

The procedure of example 1 was repeated for synthesis of various diazaoctanediamides where a given N,N'-dialkylethylenediamine is reacted with different alkyl substituted chloroacetamide. They are indicated in Table 1,

TABLE 1

| Sr. No. | Example | N,N' dialkylethylenediamine Alkyl | N,N,diakyl-2-chloroacetamide Alkyl |
|---|---|---|---|
| 1 | II | Methyl | a. isobutyl<br>b. hexyl<br>c. 2-ethylhexyl |

TABLE 1-continued

| Sr. No. | Example | N,N' dialkylethylenediamine Alkyl | N,N,diakyl-2-chloroacetamide Alkyl |
|---|---|---|---|
| 2 | III | Ethyl | a. isobutyl<br>b. hexyl<br>c. 2-ethylhexyl |
| 3 | IV | Propyl | a. isobutyl<br>b. hexyl<br>c. 2-ethylhexyl |
| 4 | V | Butyl | a. isobutyl<br>b. hexyl<br>c. 2-ethylhexyl |
| 5 | VI | Pentyl | a. isobutyl<br>b. hexyl<br>c. 2-ethylhexyl |

Example VII

In this example, use is made as the solvent formed by dissolving N,N,N',N'-tetra (2-ethylhexyl) 3,6-(N", N'''dibutyl)diaza-octane 1,8 diamide in 1-octanol to a concentration of 0.1M.

To perform extraction, this organic solvent is brought into contact with nitric acid solution at pH 2.5 containing 1 mg/l Am, 50 mg/l Eu, 200 mg/l La, 200 mg/l Ce, 0.25 M $NaNO_3$. After agitation for 30 minutes, and the decantation of two phases, the americium and lanthanides content of each phase is measured to determine the distribution co-efficients and separation factors. All experiments are carried out at aqueous to organic phase ratio of one and at ambient conditions.

Table 2 shows the results of the extraction studies.

TABLE 2

| Sr. No. | Elements | Distribution co-efficient DM | Separation Factor (DAm/DLn's) |
|---|---|---|---|
| 1 | Am | 1.58 | |
| 2. | Eu | 0.13 | 12.15 |
| 3. | Ce | 0.333 | 47.87 |
| 4. | La | 0.023 | 68.70 |

The other preferred compound namely N,N,N',N'-tetra(2-ethylhexyl) 3,6-(N",N'''dipentyl)diaza-octane 1,8 diamide has shown similar extraction behaviour.

On the basis of these results, it can be seen that the extractants of present invention can be a suitable ingredient for the separation of trivalent actinides from lanthanides.

| Reference | Extraction of... | Extractant with soft donor (prior art) (Nitrogen donor) | Extractant with hard donor (prior art) (Oxygen donor) |
|---|---|---|---|
| M. Bonnin, C. Musikas, P. Vitorge (U.S. Pat. No. 4,496,523) FIG. 1 | Am(III) At 0.117M $HNO_3$ | 0.01M TPTZ/ Tert. butyl benzene $D_{Am}=0.001$ % Extraction = $10^{-4}$ | 0.01M HDNNS/ Tert. butyl benzene $D_{Am}=500$ % Extraction = 99.8 |
| | Eu(III) At 0.117M $HNO_3$ | TPTZ $D_{Eu}=0.001$ % Extraction = $10^{-4}$ | HDNNS $D_{Eu}=500$ % Extraction = 99.8 |

| Reference | Extraction of... | Extractant with soft donor (prior art) (Sulphur donor) | Extractant with hard donor (prior art) (Oxygen donor) |
|---|---|---|---|
| R. Fitoussi, C. Musikas, (U.S. Pat. No. 4,461,747) FIG. 1 | Am(III) At 0.05M $HNO_3$ | 1.0M HDEHDTP/ n-dodecane $D_{Am}=0.01$ % Extraction < $10^{-2}$ | 1.0M TBP/ n-dodecane $D_{Am}=0.001$ % Extraction = $10^{-4}$ |
| | Eu(III) At 0.05M $HNO_3$ | 1.0M HDEHDTP/ n-dodecane $D_{Am}=0.01$ % Extraction < $10^{-2}$ | 1.0M TBP/ n-dodecane $D_{Am}=0.001$ % Extraction = $10^{-4}$ |
| G. Modolo, R. Odoj. Solv. Extr. Ion. Exch. 17(1), 33-53, 1999. (FIG. 3) | Am(III) At pH = 1.6, 1M $NaNO_3$ | di(p-chlorphenyl) dithiophosphinic acid/ toluene $D_{Am} < 1.0 \times 10^{-3}$ % Extraction < $10^{-4}$ | 1.0M TBP/ n-dodecane $D_{Am} < 1.0 \times 10^{-3}$ % Extraction < $10^{-4}$ |
| | Eu(III) At pH = 1.6, 1M $NaNO_3$ | di(p-chlorphenyl) dithiophosphinic acid/ toluene $D_{Am} < 1.0 \times 10^{-3}$ % Extraction < $10^{-4}$ | 1.0M TBP/ n-dodecane $D_{Am} < 1.0 \times 10^{-3}$ % Extraction < $10^{-4}$ |

Note:
No separation of Am from Eu is achieved when the above soft donor extractants and hard donor extractants are used independently.

| Reference | Extraction of... | Extractant with soft donor (prior art) (Sulphur donor) | Extractant with hard donor (prior art) (Oxygen donor) |
|---|---|---|---|
| Y. Zhu, J. Chen and Rongzhou Jiao Solv. Extr. Ion Exch. 14(1), 61-68, 1996. {FIG. 1) | Am(III) At pH = 3.0, 1M $NaNO_3$ | 0.5M Cyanex-301/kerosene $D_{Am}=0.4$ % Extraction = 28.0 | — |
| | Eu(III) At pH = 4.0, 1M $NaNO_3$ | 0.5M Cyanex-301/kerosene $D_{Eu}=0.1$ % Extraction = 9.0 | — |

| Reference | Extraction of... | Extractant with soft and hard donor Dialkyldiaza tetraalkyloctane-diamides (DADA) |
|---|---|---|
| Present Invention | Am and Eu, at 0.25M $NaNO_3$ and pH = 2.5 | 0.1M DADA/1-octanol $D_{Am}=1.58$ % Extraction = 62.0 $D_{Eu}=0.13$ % Extraction = 11.4 |

Comparison of extraction behavior of the extractants under similar condition and to bring them on a single scale is difficult as different extractants work in different conditions like feed composition, salt concentration, extractant concentration, pH, diluents etc.

The invention claimed is:
1. A lipophilic extractant capable of selectively extracting trivalent actinides from lanthanide ions, represented by the following structural formula:

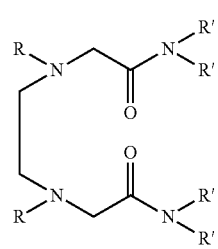

wherein R is a $C_4$ to $C_5$ normal alkyl and R' is a $C_4$ to $C_8$ normal and branched alkyl group.

2. A process for the preparation of lipophilic extractant represented by the following structural formula:

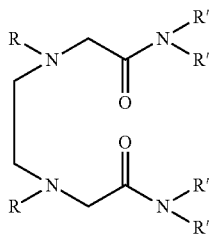

wherein R is a $C_4$ to $C_5$ normal alkyl and R' is a $C_4$ to $C_8$ normal and branched alkyl group;
the process comprising:
condensing one mole of N,N'-dialkylethylenediamine of structural formula:

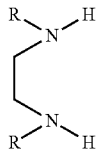

with 2.2 to 5.0 moles of N,N-dialkyl-2-chloroacetamide of structural formula:

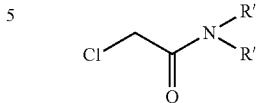

in the presence of 2.2 to 10 moles of triethylamine as a reaction mixture;
diluting the reaction mixture with xylene and neutralizing with 1.0M hydrochloric acid to produce an organic phase;
separating the organic phase and washing it with water and 2.0% sodium carbonate solution and further washing it with water to neutral pH;
drying the organic phase with anhydrous sodium sulphate and concentrating by distillation under reduced pressure to produce a residue;
distilling the residue at 120° C. under vacuum of about 1.0 millitorr using centrifugal molecular distillation unit to remove unreacted N,N-dialkyl-2-chloroacetamide;
obtaining the lipophilic extractant at a purity of about 96%.
3. The process as claimed in claim 2, being carried out at a temperature of 60-85° C. for 48 hrs in $N_2$ atmosphere.

* * * * *